US010220388B2

(12) United States Patent
Tang et al.

(10) Patent No.: US 10,220,388 B2
(45) Date of Patent: Mar. 5, 2019

(54) CENTRIFUGAL MICROFLUIDIC CONTROL SYSTEMS AND METHOD FOR CONFIGURING THE SAME

(71) Applicants: The Chinese University of Hong Kong, Hong Kong (CN); Nanjing University, Nanjing, Jiangsu (CN)

(72) Inventors: Minghui Tang, Hong Kong (CN); Ho-Pui Ho, Hong Kong (CN); Guanghui Wang, Nanjing (CN); Siu-Kai Kong, Hong Kong (CN); Fong-Chuen Loo, Hong Kong (CN); Ho Chin Kwok, Hong Kong (CN); Shu-Yuen Wu, Hong Kong (CN); Xuping Zhang, Nanjing (CN)

(73) Assignees: The Chinese University of Hong Kong, Shatin (HK); Nanjing University, Nanjing (CN)

( * ) Notice: Subject to any disclaimer, the term of this patent is extended or adjusted under 35 U.S.C. 154(b) by 139 days.

(21) Appl. No.: 15/231,500

(22) Filed: Aug. 8, 2016

(65) Prior Publication Data
US 2018/0036728 A1    Feb. 8, 2018

(51) Int. Cl.
*G01N 1/28* (2006.01)
*B01L 3/00* (2006.01)
*G01N 1/00* (2006.01)
*B04B 5/04* (2006.01)

(52) U.S. Cl.
CPC ......... *B01L 3/50273* (2013.01); *B01L 3/5021* (2013.01); *G01N 1/28* (2013.01); *B01L 2200/12* (2013.01); *B01L 2200/14* (2013.01); *B01L 2300/023* (2013.01); *B01L 2300/0609* (2013.01); *B01L 2300/0816* (2013.01); *B01L 2300/0832* (2013.01); *B01L 2300/0867* (2013.01); *B01L 2400/0409* (2013.01); *B01L 2400/0457* (2013.01); *B04B 5/0414* (2013.01)

(58) Field of Classification Search
CPC .... B01L 3/50273; B01L 3/5027; B01L 3/502; B01L 3/50; G01N 1/28; G01N 1/00
USPC .................................. 422/946, 506; 436/174
See application file for complete search history.

(56) References Cited

U.S. PATENT DOCUMENTS

2012/0302128 A1*  11/2012  McClintock ......... A63H 33/005
                                                446/431
2013/0041236 A1*   2/2013  Pugia ................. A61B 10/0045
                                                600/309

OTHER PUBLICATIONS

Tang, Minghui et al, Motor-assisted chip-in-a-tube (MACT): a new 2-and 3-dimensional centrifugal microfluidic platform for biomedical applications, Lab Chip, 17, 2017, 474-483. (Year: 2017).*

* cited by examiner

*Primary Examiner* — Christine T Mui
(74) *Attorney, Agent, or Firm* — Seed IP Law Group LLP (57) ABSTRACT

The disclosure provides a centrifugal microfluidics control system and a method configuring the same. The system may comprise a centrifugal tube; a centrifugal unit for accommodating the centrifugal tube and providing a centrifugal force to the centrifugal tube; a control unit fixed in bottom of the centrifugal tube; and a microfluidic supporting unit coupled to the control unit in the centrifugal tube. The control unit may change an orientation of the microfluidic supporting unit to change a direction of the centrifugal force applied to the microfluidic supporting unit.

17 Claims, 6 Drawing Sheets

CENTRIFUGAL MICROFLUIDIC CONTROL SYSTEMS AND METHOD FOR CONFIGURING THE SAME

TECHNICAL FIELD

The present disclosure generally relates to a centrifugal microfluidic control system, more particularly, to a centrifugal microfluidic control system, which is capable providing more than two freedoms for fluidic manipulation. In addition, the present disclosure further relates to a method for configuring the centrifugal microfluidic control system to enable the system to provide more than two freedoms for fluidic manipulation.

BACKGROUND

In recent years, centrifugal microfluidic or lab-on-a-disc (LOAD) system which aims at integrating tedious benchtop assays into one chip plays a more and more important role in point-of-care diagnostics, drug discovery and food analysis. However, on one hand, as the direction of the centrifugal force on the chip is always radially outward, the freedom of fluid manipulation in the LOAD system is limited. Besides, because the radius limitations and the flow direction are always away from the rotation center, large-scale assays integration on the disc-shaped chip is also difficult.

To add a new degree of freedom for fluidic manipulation, many systems have been developed in centrifugal microfluidic field. These systems comprise multi-manipulation strategies induced LOAD platforms such as active pressure pump or optical manipulation induced LOAD systems, chip orientation changeable LOAD system such as speed actuated inertial mechanical structure induced LOAD system or articulated centrifugal platform and so on. However, almost all these methods make the system more expensive and complicated, which increases the market entry barrier and increases the difficulty of point-of-care. Furthermore, the rotation system in the LOAD system is cumbersome compared with the disc-shaped chip, which sacrifices the portability of LOAD systems. Also, there is no unified specification in the design of these rotation systems, which also increases the market entry barrier.

To solve these problems, a lab-tube system and a lab on DVDs system have been suggested, which are more universal and portable. However, these lab-tube or lab on DVDs systems limited the freedom of the fluidic manipulation, which in turn increases the difficulty of implementation of bioassays in this system.

SUMMARY

The present disclosure provides a centrifugal microfluidic control system, which integrates a microfluidic supporting chip into a centrifugal tube to add more freedoms for fluidic manipulation, and makes the implementation of centrifugal microfluidic control easier. In addition, the commercial centrifuge may be used to provide a pumping force, which makes the system more universal and portable and decreases the market entering barrier.

On the other hand, the present disclosure enables 3D centrifugal microfluidic manipulation to be implemented. 3D centrifugal microfluidic control is very useful as different steps in different layers will not only make the integrations of the whole assay possible but also avoid the cross contamination between different steps. It gives more space for large-scale integration and may be a possible solution for addressing the limitation of space in centrifugal microfluidic tube.

The basic principle of this system is to integrate microfluidic supporting chip into a centrifugal tube. In this system, for example, the commercial available centrifuge may be used to provide the pumping force, which makes the system more universal and portable. Besides, as this chip in a tube system is completely closed, the safety of processing of infectious samples can be ensured, even outside a biological safety laboratory. In addition, in this platform, a small wireless controlled stepper motor may be introduced into the tube to change the orientation of the chip in real time and add more freedom for fluidic manipulation. This brings the concept of the 3D centrifugal microfluidic control.

According to an aspect of the present disclosure, a centrifugal microfluidic control system may comprise a centrifugal tube, a centrifugal unit, a control unit and a microfluidic supporting unit. The centrifugal unit may accommodate the centrifugal tube and provide a centrifugal force to the centrifugal tube. The control unit is fixed in bottom of the centrifugal tube. The microfluidic supporting unit is coupled to the control unit in the centrifugal tube. The control unit may change an orientation of the microfluidic supporting unit to change a direction of the centrifugal force applied to the microfluidic supporting unit.

According to an embodiment of the disclosure, the microfluidic supporting unit may comprise a microfluidic supporting chip or microfluidic supporting cube. The orientation of the microfluidic supporting chip or cube may be changed to change a direction of the centrifugal force applied thereto. As an example, the microfluidic supporting chip or cube may be made of polydimethylsiloxane, glass, plastic, silicon, polymer and the like.

According to an embodiment of the disclosure, the centrifugal unit may be a centrifuge widely used in the lab and hospital. The centrifugal unit may comprise a holder with a space for receiving the centrifugal tube; and an actuator configured to actuate the centrifugal unit to provide the centrifugal force to the microfluidic supporting chip.

According to an embodiment of the disclosure, the system may further comprise a communication unit for communicating signals to the control unit. The control unit may change the orientation of the microfluidic supporting unit in response to the signals from the communication unit. The control unit may comprise a wirelessly controlled stepper motor fixed in the bottom of the centrifugal unit. The microfluidic supporting chip then can be inserted on the stepper motor.

According to an embodiment of the disclosure, the microfluidic supporting chip may comprise one microfluidic supporting layer in a 2D application and comprise two or more microfluidic supporting layers in a 3D application. Each of the microfluidic supporting layers can comprise a plurality of chambers for accommodating samples and/or reagents and at least one passage for allowing the samples and/or reagents to flow between the chambers. The microfluidic supporting layers can comprise a filtering membrane or barrier membrane for removing undesired impurities or containing the desire component. In the case that the microfluidic supporting chip comprises two or more layers, at least one channel is provided between adjacent microfluidic supporting layers to fluidly communicate the adjacent layers such that different steps can be operated in different layers.

According to an further aspect of the present disclosure, a method for configuring a centrifugal microfluidic control system may comprise accommodating a centrifugal tube in a centrifugal unit for providing a centrifugal force to the centrifugal tube; fixing a control unit into a bottom of the centrifugal tube; coupling a microfluidic supporting unit to the control unit in the centrifugal tube, and changing, by the control unit, an orientation of the microfluidic supporting unit to change a direction of the centrifugal force applied to the microfluidic supporting unit.

According to an embodiment of the disclosure, the microfluidic supporting unit may comprise a microfluidic supporting chip with two or more microfluidic supporting layers. The method may further comprise placing the microfluidic supporting chip into the centrifugal tube. The microfluidic supporting chip is therefore coupled to the control unit.

According to an embodiment of the disclosure, the centrifugal unit may be a centrifuge widely used in lab and hospitals and can comprise a holder and an actuator. The method may further comprise a step of receiving the centrifugal tube into the holder and actuating the actuator to provide the centrifugal force to the microfluidic supporting chip.

According to an embodiment of the disclosure, the method may further comprise a step of communicating signals to the control unit by a communication unit, and changing the orientation of the microfluidic unit in response to the signals from the communication unit.

According to an embodiment of the disclosure, the method may further comprise providing samples to be treated and/or proper reagents on one of the microfluidic supporting layers; transporting an intermediate product obtained from the samples and/or reagents to an adjacent one of the microfluidic supporting layers; and providing other reagents on said adjacent one of the microfluidic supporting layers.

According to an embodiment of the disclosure, the method can further comprise forming a plurality of chambers on each of the microfluidic supporting layers for accommodating the samples and/or reagents; and providing at least one passage between the plurality of chambers for allowing the samples and/or reagents to flow therebetween.

According to an embodiment of the disclosure, the adjacent microfluidic supporting layers can be configured with at least one channel therebetween to fluidly communicate the adjacent microfluidic supporting layers to perform different step in different layers.

BRIEF DESCRIPTIONS OF DRAWINGS

Exemplary non-limiting embodiments of the present disclosure are described below with reference to the attached drawings. The drawings are illustrative and generally not to an exact scale. The same or similar elements on different figures are referenced with the same reference numbers.

DETAILED DESCRIPTIONS

Reference will now be made in detail to some specific embodiments of the disclosure including the best modes contemplated by the inventors for carrying out the disclosure. Examples of these specific embodiments are illustrated in the accompanying drawings. While the disclosure is described in conjunction with these specific embodiments, it will be understood that it is not intended to limit the disclosure to the described embodiments. On the contrary, it is intended to cover alternatives, modifications, and equivalents as may be included within the spirit and scope of the disclosure as defined by the appended claims. In the following description, numerous specific details are set forth in order to provide a thorough understanding of the present disclosure. The present disclosure may be practiced without some or all of these specific details. In other instances, well-known process operations have not been described in detail in order not to unnecessarily obscure the present disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 1:
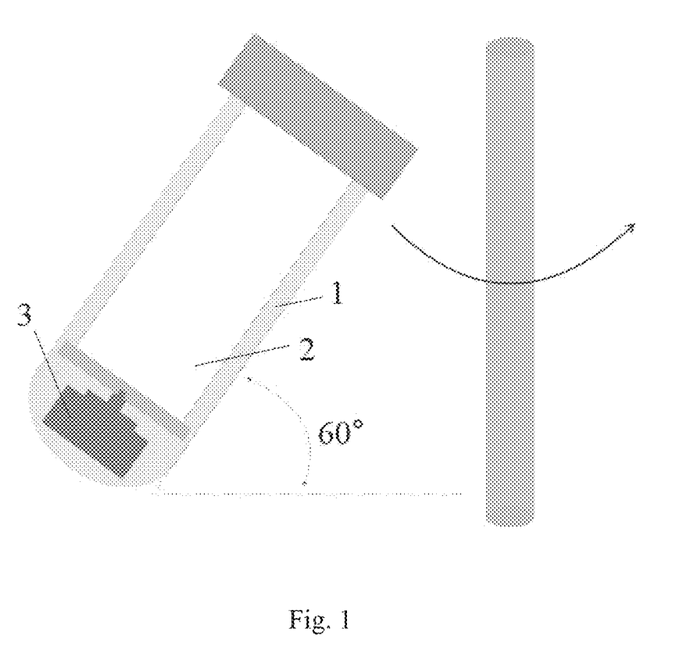
FIG. 1 illustrates a schematic structure of a centrifugal microfluidic control system according to an embodiment of the present disclosure.

FIG. 1 illustrates a schematic structure of a centrifugal tube according to an embodiment of the present disclosure, in which the centrifuge for providing centrifugal field is not shown. The centrifuge may be a commercial centrifuge widely used in biology labs or hospitals, and thus increase the universality and applicability of the centrifugal microfluidic control system of the present disclosure. In addition, the platform of the present disclosure is based on tubes, therefore solves a technical issues that standard of the platform of the centrifugal microfluidic control is not uniform.

As shown in FIG. 1, centrifugal microfluidic control system may comprise a centrifugal tube 1, a centrifugal unit (not shown), a microfluidic supporting unit 2 and a control unit 3. The centrifugal unit may be a commercial available centrifuge that is widely used in biology labs or hospitals, and here will not describe it in detail. The centrifugal unit may be used to accommodate the centrifugal tube 1 and provide a centrifugal force to the centrifugal tube 1. The centrifugal tube may be any of plastic centrifuge tube, glass centrifugal tube, steel centrifugal tube or any other centrifugal tube that may be available. In the present disclosure, since the microfluidic supporting unit 2 is actuated by a motor in a tube, the present disclosure may be seemed as a motor asslysisd chip in a tube (MACT) system.

The microfluidic supporting unit 2 is coupled to an upper side of the control unit 3 and the control unit 3 may be placed in the centrifugal tube 1. In a 2D centrifugal microfluidic control, the microfluidic supporting unit 2 may comprise a microfluidic supporting chip or a microfluidic supporting cube with one microfluidic supporting layer, and may comprise a microfluidic supporting chip with two or more microfluidic supporting layers for performing different steps in different layers in a 3D centrifugal microfluidic control. For example, the microfluidic supporting chip or cube may be made of polydimethylsiloxane, glass, plastic, silicon, polymer and the like. However, the microfluidic supporting chip may also be made of any other proper material. When the microfluidic supporting unit 2 comprises two or more microfluidic supporting layers, as the direction of centrifugal force can be perpendicular to the surface of the microfluidic supporting unit 2 (i.e. microfluidic supporting chip), centrifugal force can drive the fluid from the upper layer into the next layer, which brings the concept of the 3D centrifugal microfluidic control.

When the centrifugal microfluidic control system operates, a microfluidic supporting unit 2 is placed into a holder of a centrifugal unit which provides a space for receiving the centrifugal tube. Then an actuator of the centrifugal unit actuates the centrifugal tube to provide a centrifugal force thereto.

To make the function of the centrifugal microfluidic control system more clarity, two specific disclosures, human blood plasma separation and bacterium plasmid DNA extraction which are very often used samples, are described as below. However, it should be understand that the above mentioned applications are only examples and not limit the scope of the present disclosure.

The control unit 3 is fixed in a bottom of the centrifugal tube 1 for providing driving force to drive the microfluidic supporting unit 2 to rotate. Therefore, an orientation of the microfluidic supporting unit 2 can be changed and thus a direction of the centrifugal force applied onto the microfluidic supporting unit 2 is changed.

In an embodiment of the present disclosure, the control unit 3 may be a wirelessly controlled stepper motor. Here, the wirelessly controlled stepper motor in the centrifugal tube 1 may be controlled by a wireless control module (not shown) in real time. The wireless control module may send a control command to cause the stepper motor to rotate via a communication unit (not shown). As the stepper motor rotating, the centrifugal field applied on the microfluidic supporting unit 2 will be changed to make the implementation of often used operations such as bidirectional flow and inward pumping very easy.

As the control unit 3 may change the orientation of the microfluidic supporting unit 2 in real time, the direction of centrifugal force may also be perpendicular to the surface of the microfluidic supporting unit 2. As a consequence, the fluid manipulation between different layers in multilayer microfluidic supporting unit 2 becomes possible. Therefore, a 3D centrifugal microfluidic control will be achieved.

Figure 2A:
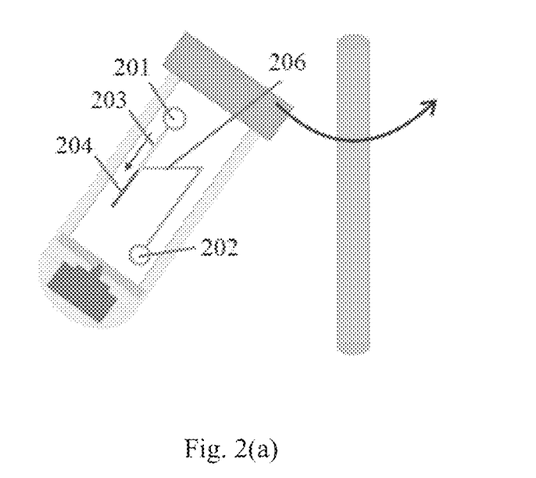
FIGS. 2(a)-2(b) show an exemplary 2D application of the centrifugal microfluidic control system according to an embodiment of the present disclosure.
Figure 2B:
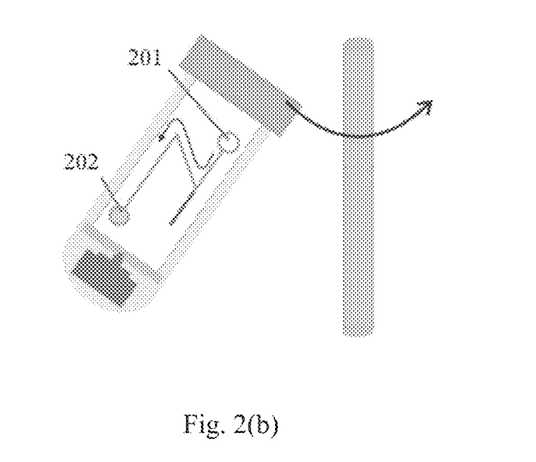

FIGS. 2(a)-2(b) show an exemplary 2D application of the centrifugal microfluidic control system according to an embodiment of the present disclosure. As shown in FIGS. 2(a)-2(b), the microfluidic supporting unit 2 may comprise chambers 201 and 202, and a passage 206 for allowing the samples and/or reagents to flow between the chambers.

In an embodiment of the present disclosure, a blood separation process is selected as an example of a 2D centrifugal microfluidic application based on this system. FIG. 2(a) illustrates that blood is fully filled in the passage and is divided into two layers based on density difference; and FIG. 2(b) illustrates that the blood plasma is got separated from the whole human blood.

In the embodiment of blood plasma separation, firstly, certain volume of human blood pretreated with the anticoagulant EDTA (Becton, Dickinson and Company) is injected into the chip. Here, 5 μl human blood pretreated with the anticoagulant EDTA is selected as an example to explain the principle of 2D centrifugal microfluidics application. However, other kind of samples may also be used and not limit to human blood. In addition, any volume of samples may be selected. Then, as the state shown in FIG. 2(a), the blood is fully filled into the passage 206 and is divided into two layers 203 and 204 due to the density difference in the centrifugal field. For the two layers 203 and 204, the supernatant 203 is plasma and the bottom layer 204 is white blood cells, red blood cells, and platelets. Then, the stepper motor is rotated 180° (FIG. 2(b)), the blood plasma is driven into the reserved chamber 202 and the separation is realized naturally. Experimental result illustrates that about 2.5 μl plasma is separated from the 5 μl human blood (without being diluted) in only 1 minute (1500 rpm) and no red cell is observed in the plasma. This separation method is effective and high repeatable.

In a 3D application, a microfluidic supporting chip with two or more microfluidic supporting layers will be used for performing different steps in different layers. As an example, in an embodiment of the present disclosure, two microfluidic supporting layers are selected to show the 3D application of the present centrifugal microfluidic control system. However, one should understand more than two microfluidic supporting layers will be applicable in other embodiments.

FIGS. 3(a)-3(l) show a whole process of an exemplary 3D application of the centrifugal microfluidic control system according to an embodiment of the present disclosure. As shown in FIG. 3(a)-3(l), the microfluidic supporting unit 2 comprises a microfluidic supporting chip having two microfluidic supporting layers 21 and 22. There are a plurality of chambers and passages provided in each of the microfluidic supporting layers 21 and 22. In addition, there is a channel (not shown) provided between the two microfluidic supporting layers 21 and 22 to fluidly communicate the adjacent layers.

As an example of 3D application of the present disclosure, bacterium plasmid DNA extraction is selected to explain the 3D control principle of the centrifugal microfluidic control system. In the embodiment of bacterium plasmid DNA extraction, the system in MACT based format mimicked a benchtop work. The microfluidic supporting chip used for DNA extraction may comprise two microfluidic supporting layers 21 and 22: the first layer 21 may be used for bacteria lysis and the second layer 22 may be used for DNA purification. Between the first layer 21 and the second layer 22, there is a channel vertical to the surface of the microfluidic supporting chip 2 throughout to fluidly communicate the adjacent layers.

As an example, plasmid DNA extraction buffer may be obtained from a DNA extraction kit. In this embodiment, there are four buffers being used, i.e. resuspension buffer composed of Tris buffer with RNase for removal of RNA contamination (buffer 1), lysis buffer composed of alkaline and detergent (buffer 2), neutralization buffer composed of acidic acetate buffer (buffer 3) and wash buffer composed of 70% ethanol (buffer 4). Chemically competent Bacteria *E. coli* DH5(alpha) (Life Technologies) may be transformed with plasmid DNA from Synthetic Biology Part Registry's Repository biobrick BBa_E0040, which contains the coding gene of green fluorescent protein derived from jellyflysis *Aequeora victoria* wild-type GFP, in the synthetic biology plasmid vector pSB1A2, under 42 Degrees Celsius 1 min heat shock followed by overnight incubation in LB agar plate with 50 μg/mL ampicillin. A single colony may be picked and inoculated into liquid LB medium sparked with 50 μg/mL ampicillin and growth for 12 hours before plasmid DNA extraction.

The process of plasmid DNA extraction from bacteria based on MACT system will be described as below referring to FIGS. 3(a)-3(l).

Figure 3A:
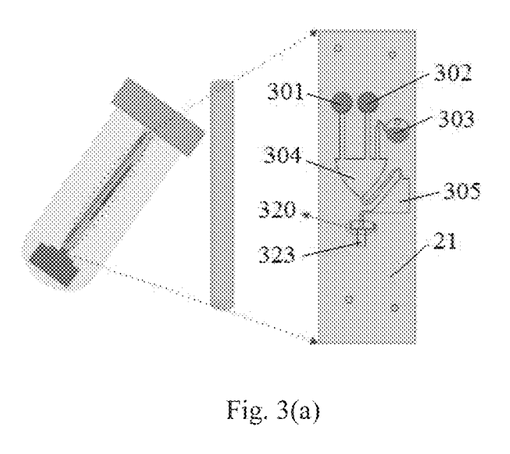
FIGS. 3(a)-3(l) show a whole process of an exemplary 3D application of the centrifugal microfluidic control system according to an embodiment of the present disclosure.

The process begins with Step 1, in which certain volume of a sample, proper volume of a lysis buffer and proper volume a neutralization buffer may be injected into the corresponding chambers 301, 302, and 303 on the first layer of the microfluidic supporting chip, respectively, as shown in FIG. 3(a). For purpose of explanation, here 15 μl sample, 15 μl lysis buffer and 21 μl neutralization buffer are selected as an example and the initial orientation of the microfluidic supporting chip may be determined as that shown in FIG. 3(a). It should be understood other proper volume of sample, lysis buffer and neutralization buffer may also be used without going beyond the scope of the present disclosure.

Figure 3B:
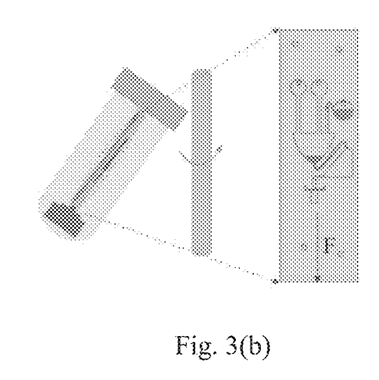

As shown in FIG. 3(b), in Step 2, the sample and lysis buffer may flow into a mixing chamber 304 by gravity and the centrifugal force F for mixing at a proper rotation speed, for example, 5-50 rpm. It should be appreciated that the rotation speed of the control unit (motor) 3 may be different for different application.

Figure 3C:
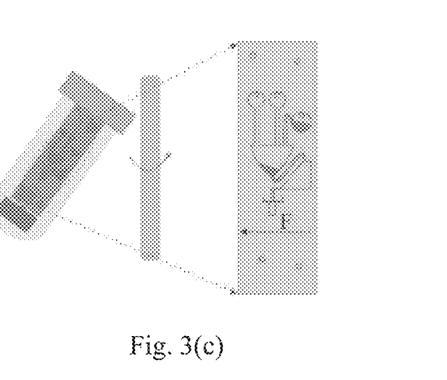

The process proceeds to Step 3, and the direction of the centrifugal force F is changed which is shown in FIG. 3(c). In this step, the orientation of the microfluidic supporting chip 2 may be changed by 90° alternately, for example at 30 rpm between the states of FIGS. 3(b) and 3(c) for some times (such as 5 times) to make the mixing sufficiently.

Figure 3D:
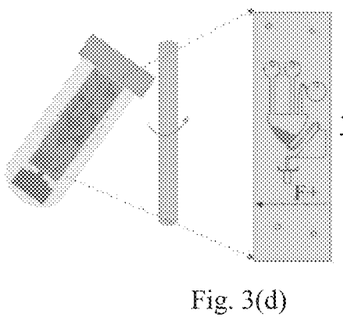

FIG. 3(d) illustrates that in Step 4, the orientation of the microfluidic supporting chip changes by 90°, such that the direction of the centrifugal force F is changed. In this Step, the neutralization buffer is injected into the mixing chamber 304. As the orientation of the microfluidic supporting chip is changed at a rotate speed sufficient to cause the neutralization buffer contained in the chamber 303 to flow into the mixing chamber 304, and thus the neutralization buffer is also driven into the mixing chamber 304.

Figure 3E:
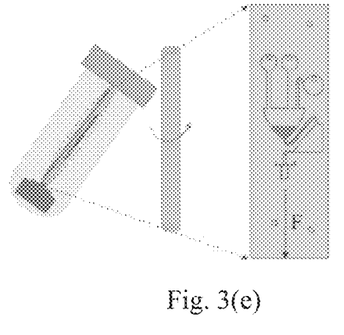

Then the process proceeds to Step 5 as shown in FIG. 3(e), and the direction of the centrifugal force F is changed. In this step, the orientation of the microfluidic supporting chip 2 may be changed by 90° alternately in a proper rotate speed (e.g. 30 rpm) between the states of FIGS. 3(d) and 3(e) for some times (e.g. 5-10 times) to make the mixing sufficient. In this step, the rotate speed will not cause the mixed fluid flowing out of the mixing chamber 304. As a consequence, protein-genomic DNA aggregate may be formed in this step.

Figure 3F:
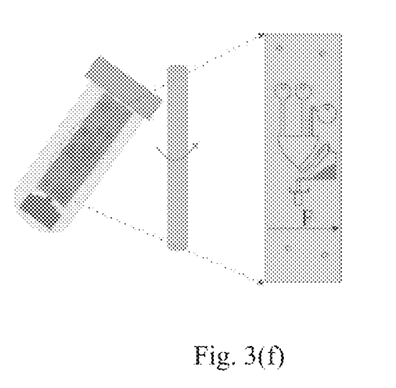

In Step 6, after the sample, the lysis buffer and the neutralization buffer are fully mixed, as shown in FIG. 3(f), the orientation of the microfluidic supporting chip 2 is changed by 180° relative to that shown in FIG. 3(d) such that the direction of the centrifugal force F is changed and all of the above mixed fluid may be driven into a buffer chamber 305 at a proper rotate speed which is sufficient to cause the mixed fluid to flow out of the mixing chamber 304, for example, at 60 rpm in this embodiment.

Figure 3G:
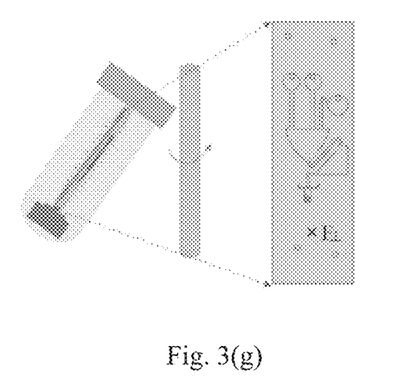
Figure 3H:
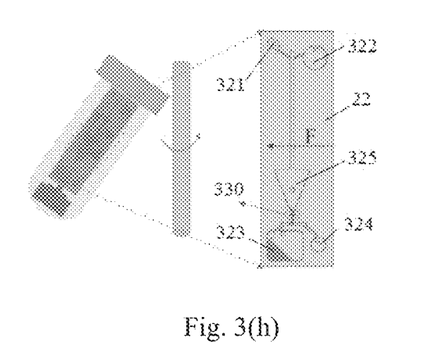

FIG. 3(g) illustrates an operation of Step 7. As shown in FIG. 3 (g) the microfluidic supporting chip 2 is driven to rotate to be perpendicular to the direction of the centrifugal force F. Therefore, all of the fluid may be driven into a second layer with the help of the centrifugal force at proper rotate speed (e.g. 50 rpm) via the channel between the two layers, while the insoluble factor including protein-genomic DNA aggregate may be removed by a paper filter 320. As shown in FIG. 3(h), in this embodiment, the second microfluidic supporting layer 22 may comprise a chamber 321 for accommodating an elution buffer, a chamber 322 for accommodating a wash buffer, a waste chamber 323 for accommodating undesired fluid, and a yielding chamber 324 for receiving the plasmid DNA.

Then in Step 8, the process begins to proceed in the second microfluidic supporting layer 22 shown in FIG. 3(h). In this step, the orientation of the microfluidic supporting chip 2 is changed by 90° relative to that in Step 7. As shown in FIG. 3(h), the second layer 22 may also comprise a plurality of chambers and passages for allowing communication between the chambers. In addition, the second microfluidic supporting layer 22 may further comprise a barrier membrane 330 for containing plasmid DNA. The barrier membrane 330 may for example be a lab-made silica gel membrane. In addition, the barrier membrane 330 may be any other material that is able to contain the plasmid DNA and allow other components to flow through. As the process proceeds, the mixed fluid without impurities in this step may be driven into a waste chamber 323 at a proper rotate speed (e.g. 100 rpm), while plasmid DNA may be bound to the barrier membrane 330.

Figure 3I:
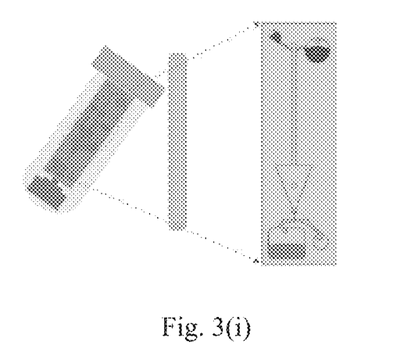

FIG. 3(i) illustrates an operation of Step 9 for processing the plasmid DNA contained in the barrier membrane 330. During the operation of Step 9, a volume of wash buffer and corresponding volume of elution buffer may be injected into the corresponding chambers 321 and 322 in the second layer 22, respectively. As an example, 44 μl wash buffer and 10 μl elution buffer may be injected into the corresponding chamber 321 and 322.

Figure 3J:
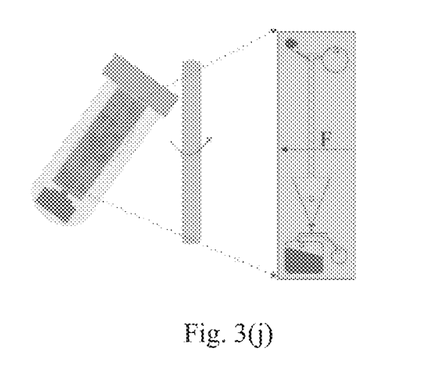

Then the process proceeds to Step 10 shown in FIG. 3(j). In Step 10, the wash buffer may be driven into the waste chamber 323 at proper rotate speed (e.g. 100 rpm) due to the centrifugal force F, and thus cause the barrier membrane 330 to contain the plasmid DNA to be washed.

Figure 3K:
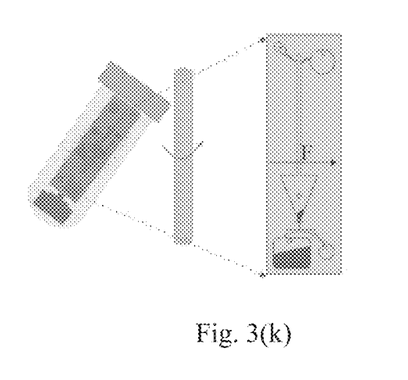

As shown in FIG. 3(k), the orientation of the microfluidic supporting chip 2 then is changed by 180° relative to that in Step 10 such that the direction of the centrifugal force F is changed. In this step 11, the elution buffer may be driven to soak the barrier membrane for a period time at a proper rotate speed, for example at 50 rpm and for 1 minute.

Figure 3L:
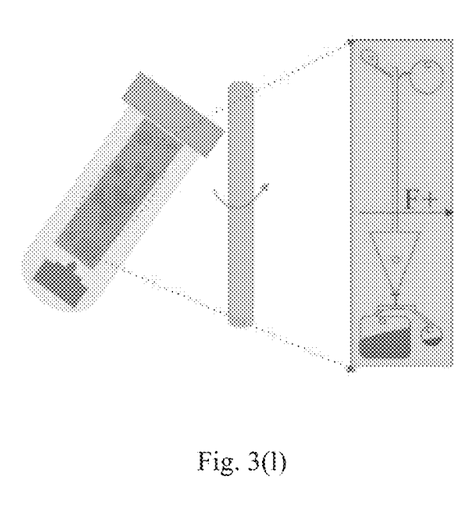

As shown in FIG. 3(l), in the orientation of Step 11, the elution buffer carrying the plasmid DNA may be driven into the yielding chamber 324 at proper rotate speed, for example, at 200 rpm. Then the process for extracting the plasmid DNA is completed.

In this plasmid DNA extraction assay, the insoluble factor including protein-genomic DNA aggregate may be removed by the filter paper 320 when the reagent flows through it. Plasmid DNA may be first bound to the barrier membrane 330 which may be prepared for example by adding 2 μL of 100 mg/mL (optimized silica amount,) silica gel (Sigma-Aldrich, pore size 60 Å) in between two polycarbonate membrane (Sterlitech, pore size 0.01 μm). Then, the wash buffer may flow through the barrier membrane to get the DNA washed.

The detail structure and principle of the present disclosure have been described in different exemplary embodiments. The new system solves the problem that there is no uniform standard of the centrifugal microfluidics control platform. The present system is based on a tube, which means that the centrifuge widely used in a biological lab or hospital may be used to construct the centrifugal microfluidics control platform, thereby the applicability and universality is increased largely.

As described in the above, the current system is able to change the orientation of the microfluidics supporting chip in real time, such that the direction of the centrifugal force applied onto the chip may be changed. That is to say, 3D centrifugal microfluidics control becomes possible. In this aspect, this system may overcome the limited manipulation freedom of the common centrifugal microfluidics control platform. Thus application scope of the system is increased.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment is chosen and described in order to best explain the principles of the disclosure and the practical application, and to enable others of ordinary skill in the art to understand the disclosure for various embodiments with various modifications as are suited to the particular use contemplated.

What is claimed is:

1. A centrifugal microfluidics control system, comprising:
a centrifugal tube;
a centrifugal unit accommodating the centrifugal tube and providing a centrifugal force to the centrifugal tube;
a control unit fixed in the bottom of the centrifugal tube; and
a microfluidic supporting unit coupled to the control unit in the centrifugal tube, the microfluidic supporting unit and the control unit being arranged inside the tube,
wherein the control unit changes an orientation of the microfluidic supporting unit to change a direction of the centrifugal force applied to the microfluidic supporting unit.

2. The system according to claim 1, wherein the microfluidic supporting unit comprises a microfluidic supporting chip or microfluidic supporting cube.

3. The system according to claim 2, wherein the microfluidic supporting chip or cube is made of polydimethylsiloxane.

4. The system according to claim 1, wherein the centrifugal unit comprises:
a holder with a space receiving the centrifugal tube; and
an actuator configured to actuate the centrifugal unit to provide the centrifugal force.

5. The system according to claim 1, wherein the system further comprises:
a communication unit communicating signals to the control unit, the control unit changing the orientation of the microfluidic supporting unit in response to the signals.

6. The system according to claim 5, wherein the control unit comprises a wirelessly controlled stepper motor fixed in the bottom of the centrifugal unit.

7. The system according to claim 2, wherein the microfluidic supporting chip comprises at least two microfluidic supporting layers.

8. The system according to claim 7, wherein each of the microfluidic supporting layers comprises a plurality of chambers for accommodating samples and/or reagents and at least one passage allowing the samples and/or reagents to flow between the chambers.

9. The system according to claim 7, wherein at least one channel is provided between adjacent microfluidic supporting layers to fluidly communicate the adjacent microfluidic supporting layers.

10. A method for configuring a centrifugal microfluidic system, comprising:
accommodating a centrifugal tube in a centrifugal unit for providing a centrifugal force to the centrifugal tube;
fixing a control unit into a bottom of the centrifugal tube;
coupling a microfluidic supporting unit to the control unit in the centrifugal tube, the microfluidic supporting unit and the control unit being arranged inside the tube; and
changing, by the control unit, an orientation of the microfluidic supporting unit to change a direction of the centrifugal force applied to the microfluidic supporting unit.

11. The method of claim 10, wherein the microfluidic supporting unit comprises a microfluidic supporting chip with two or more microfluidic supporting layers, and the method further comprises:
placing the microfluidic supporting chip into the centrifugal tube.

12. The method of claim 11, wherein the centrifugal unit comprises a holder and an actuator, and the method further comprises:
receiving the centrifugal tube into the holder; and
actuating the actuator to provide the centrifugal force.

13. The method of claim 10, further comprising:
communicating signals to the control unit; and
changing the orientation of the microfluidic unit in response to the signals.

14. The method of claim 13, wherein the control unit comprises a wirelessly controlled stepper motor fixed in the bottom of the centrifugal unit.

15. The method of claim 11, further comprising:
providing samples to be treated and/or proper reagents on one of the microfluidic supporting layers;
transporting an intermediate product obtained from the samples and/or reagents to an adjacent one of the microfluidic supporting layers; and
providing other reagents on said adjacent one of the microfluidic supporting layers.

16. The method of claim 15, further comprising:
forming a plurality of chambers on each of the microfluidic supporting layers for accommodating the samples and/or reagents; and
providing at least one passage between the plurality of chambers for allowing the samples and/or reagents to flow therebetween.

17. The method of claim 15, wherein, the adjacent microfluidic supporting layers are configured with at least one channel therebetween to fluidly communicate the adjacent microfluidic supporting layers.

* * * * *